United States Patent
Weiss

(10) Patent No.: US 12,245,848 B2
(45) Date of Patent: Mar. 11, 2025

(54) MR IMAGING FOR RADIATION THERAPY PLANNING

(71) Applicant: KONINKLIJKE PHILIPS N.V., Eindhoven (NL)

(72) Inventor: Steffen Weiss, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 107 days.

(21) Appl. No.: 17/916,822

(22) PCT Filed: Apr. 1, 2021

(86) PCT No.: PCT/EP2021/058552
§ 371 (c)(1),
(2) Date: Oct. 4, 2022

(87) PCT Pub. No.: WO2021/204640
PCT Pub. Date: Oct. 14, 2021

(65) Prior Publication Data
US 2023/0148894 A1 May 18, 2023

(30) Foreign Application Priority Data
Apr. 6, 2020 (EP) .................................... 20168130

(51) Int. Cl.
*A61B 5/055* (2006.01)
*G01R 33/44* (2006.01)

(52) U.S. Cl.
CPC ............ *A61B 5/055* (2013.01); *G01R 33/443* (2013.01); *A61B 2576/00* (2013.01)

(58) Field of Classification Search
CPC ............ G01R 33/56563; G01R 33/443; G01R 33/4828; G01R 33/5608; A61B 2576/00; A61B 5/0037; A61B 5/055
See application file for complete search history.

(56) References Cited

U.S. PATENT DOCUMENTS 10,591,562 B2   3/2020   Boernert et al.
11,275,140 B2   3/2022   Vesanen et al.

FOREIGN PATENT DOCUMENTS

JP   2007159718 A   6/2007

OTHER PUBLICATIONS

Van Herk M, Kooy HM. Automatic Three-Dimensional Correlation of CT-CT, CT-MRI, and CT-SPECT Using Chamfer Matching. Med Phys. 1994;21:1163-1178.

(Continued)

*Primary Examiner* — Amelie R Davis

(57) ABSTRACT

The invention relates to a method of MR imaging of a body (10) of a patient positioned in an examination volume of an MR device (1). It is an object of the invention to provide a method that enables geometrically correct MR-only radiation therapy planning at minimum scan times. The method of the invention comprises the following steps: acquiring first MR imaging data representative of at least one region of the body (10); analyzing said first MR imaging data to delineate at least one anatomical structure within said body region; acquiring second MR imaging data of said body region using a multi-point Dixon sequence; deriving a B0 map from said second MR imaging data; analyzing said B0 map to determine at least one low fidelity region of said B0 map; performing B0 mapping to refine the B0 map using a multi-acquisition gradient echo sequence restricted to at least one region where said delineated anatomical structure and said low fidelity region overlap completely or partially; and correcting geometrical distortions in said first and/or second MR imaging data using the refined B0 map. Moreover, the invention relates to a MR device (1) for carrying out the method, and to a computer program to be executed on a MR device (1).

19 Claims, 3 Drawing Sheets

(56) References Cited

OTHER PUBLICATIONS

Brock KK. Results of a Multi-Institution Deformable Registration Accuracy Study (Midras). Int J of Radiation Oncology Biology Physics. 2010;76:583-596.
Wang D, Doddrell DM, Cowin G. A Novel Phantom and Method for Comprehensive 3-Dimensional Measurement and Correction of Geometric Distortion in Magnetic Resonance Imaging. Magn Reson Imag. 2004;22:529-542.
Torfeh T, Hammoud R, Perkins G, et al. Characterization of 3D Geometric Distortion of Magnetic Resonance Imaging Scanners Commissioned for Radiation Therapy Planning. Magn Reson Imag. 2016;34:645-653.
Wang H, Balter J, Cao Y. Patient-Induced Susceptibility Effect on Geometric Distortion of Clinical Brain MRI for Radiation Treatment Planning on a 3T Scanner. Phys Med Biol. 2013;58:465.
Weiss S, Nejad-Davarani S, Eggers H, Orasanu E, Renisch S, Glide-Hurst C. A novel and rapid approach to estimate patient-specific distortions based on mDIXON MRI. Phys Med Biol. Aug. 1, 2019;64(15):155002.
Berker Y, Franke J, Salomon A, et al. MRI-Based Attenuation Correction for Hybrid PET/MRI Systems: A 4-Class Tissue Segmentation Technique Using a Combined Ultrashort-Echo-Time/Dixon MRI Sequence. JNucl Med. 2012:53;796-804.
Tyagi N, Fontenla S, Zhang J, et al. Dosimetric and workflow evaluation of first commercial synthetic CT software for clinical use in pelvis. Phys Med Biol. 2017;62(8):2961-2975.
Freedman et al "Synthetic 4D-CT of the Thorax for Treatment Plan Adaptation on MR-Guided Radiotherapy Systems" Physics in Med. and Biol. Institute of Physics vol. 64, No. 11 May 23, 2019 p. 115005.
International Search Report and Written Opinion from PCT/EP2021/058552 mailed Jul. 9, 2021.

MR IMAGING FOR RADIATION THERAPY PLANNING

CROSS REFERENCE TO RELATED APPLICATIONS

This application is a U.S. national phase application of International Application No. PCT/EP2021/058552 filed Apr. 1, 2021, which claims the benefit of EP application Ser. No. 20/168,130.1 filed Apr. 6, 2020 and is incorporated herein by reference.

FIELD OF THE INVENTION

The invention relates to the field of magnetic resonance (MR) imaging. It concerns a method of MR imaging of an object positioned in an examination volume of a MR device. The invention also relates to a MR device and to a computer program to be run on a MR device.

BACKGROUND OF THE INVENTION

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

According to the MR method in general, the body of the patient to be examined is arranged in a strong, uniform magnetic field $B_0$ whose direction at the same time defines an axis (normally the z-axis) of the co-ordinate system on which the measurement is based. The magnetic field $B_0$ produces different energy levels for the individual nuclear spins in dependence on the magnetic field strength which can be excited (spin resonance) by application of an electromagnetic alternating field (RF field) of defined frequency (so-called Larmor frequency, or MR frequency). From a macroscopic point of view, the distribution of the individual nuclear spins produces an overall magnetization which can be deflected out of the state of equilibrium by application of an electromagnetic pulse of appropriate frequency (RF pulse) while the magnetic field $B_0$ extends perpendicular to the z-axis, so that the magnetization performs a precessional motion about the z-axis. The precessional motion describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°).

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of receiving RF coils which are arranged and oriented within an examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

In order to realize spatial resolution in the body, linear magnetic field gradients extending along the three main axes are superposed on the uniform magnetic field $B_0$, leading to a linear spatial dependency of the spin resonance frequency. The signal picked up in the receiving coils then contains components of different frequencies which can be associated with different locations in the body. The signal data obtained via the receiving coils corresponds to the spatial frequency domain and is called k-space data. The k-space data usually includes multiple lines acquired with different phase encoding. Each line is digitized by collecting a number of samples. A set of k-space data is converted to an MR image by means of Fourier transformation.

Radiation therapy or radiotherapy is a therapy using ionizing radiation, generally as part of cancer treatment to control or kill malignant cells. The ionizing radiation is normally delivered by a linear accelerator to treat the diseased tissue selectively and with a precisely adjusted dose. Dose calculation performed on the basis of MR imaging has been reported several years ago wherein MR imaging was used as a complimentary modality to computed tomography. However, as MR imaging provides superior soft tissue contrast and high precision in the delineation of anatomical structures to be irradiated (as compared to computed tomography), the concept of carrying out all steps of radiation therapy planning on the basis of MR imaging as the sole modality (so-called MR imaging-only radiation therapy) is becoming more and more important.

In MR-only radiation therapy planning, geometrically correct MR imaging is essential, because target tumors and organs-at-risk are delineated on the basis of MR images, and dose planning and patient positioning for therapy are performed based on these delineations. There is a strong interest to use the MR-only variant to eliminate redundant CT scans, and more importantly to avoid geometric uncertainties during CT-MR registration which have been shown to be on the order of several millimeters. Geometrical accuracy of MR images is limited by various types of distortions. System-level distortions arise from gradient nonlinearities and $B_0$ field inhomogeneities inherent to the used MR device. Both effects are largely corrected during image reconstruction based on per-system reference data. However, chemical shift of fat and magnetic susceptibility effects cause distortions that depend on the patient anatomy and thus typically require additional data acquisition to perform a correction. Spatial variations in susceptibility, most pronounced at interfaces with large susceptibility differences such as air/tissue or bone/metal, cause $B_0$ field inhomogeneities up to about 4 ppm in the human head, which can cause distortions of up to 4 mm at the sinus/tissue interface in the brain. Chemical shift and patient-specific distortions due to variations in susceptibility are commonly addressed by scanning at high read-out bandwidth. In addition, precise $B_0$ mapping using a multi-acquisition gradient echo (GRE) sequence is increasingly used to quantify and correct for such distortions that are related to $B_0$ field inhomogeneities. A multi-acquisition gradient echo sequence includes multiple radio frequency (RF) excitation pulses. Subsequent to each of the RF excitation pulse one or more gradient echoes are acquired, while subsequent to the respective RF excitations the one or more gradient echoes are acquired at different echo times. A very practical example of a multi-acquisition gradient echo sequence is a dual acquisition gradient echo sequence. Such a dual acquisition gradient echo sequence includes two successive gradient echo acquisition following respective RF excitation pulses and the gradient echoes of the respective acquisitions have different echo times. In this imaging sequence, gradient-recalled echo signal data are acquired at two different echo times and a $B_0$ map is derived from the differences in the signal phase at the two different echo times. The signal phase is proportional to the local field strength. However, this sequence requires additional scan time and image processing steps (such as phase unwrapping) to apply the corrections.

Recently, a novel and rapid approach for the assessment of image distortions in MR-only radiation therapy planning by using a $B_0$ map derived from multi-point Dixon (mDIXON) imaging has been proposed (see Weiss et al., "A novel and rapid approach to estimate patient-specific distortions based on mDIXON MRI", Phys. Med. Biol. 2019, 64(15):155002). Using mDIXON imaging is favorable since it is commonly performed for the purpose of generating synthetic CT images in the MR-only radiation therapy planning workflow (see Berker et al., "MRI-Based attenuation correction for hybrid PET/MRI systems: a 4-class tissue segmentation technique using a combined ultrashort-echo-time/Dixon MRI sequence", J. Nucl. Med. 2012, 53:796-804; Tyagi et al., "Dosimetric and workflow evaluation of first commercial synthetic CT software for clinical use in pelvis", Phys. Med. Biol. 2017, 62(8):2961-2975). This dual use of the mDIXON MR imaging data also results in an inherent simultaneous acquisition of $B_0$ maps and radiation therapy planning data, which minimizes the risk of misalignments due to patient motion. As for distortion correction, the mDIXON approach allows to correct for a large fraction of patient-specific distortions using the mDIXON-based $B_0$ map only. Because this field map is estimated within the mDIXON reconstruction for the purpose of water/fat separation as required in CT-simulation, the respective correction saves the complete scan time for a dedicated field mapping step, which is typically 2-4 minutes and thus more than the scan time of the mDIXON scan itself.

However, it turns out that the reduction of the scan time when using the mDIXON-based $B_0$ mapping approach is at the expense of a reduced fidelity of the $B_0$ map (see article by Weiss et al. cited above). While the differences between distortions derived from mDIXON imaging on the one hand and distortions derived from dedicated $B_0$ mapping is globally much smaller than the total distortion estimated by pure $B_0$ mapping, almost all differences larger than 50% observed between the two approaches occur very localized in regions with high spatial variation of $B_0$. These local errors in distortion estimation become important if they occur at the locations to be treated by radiation therapy. A tumor may not be subjected to the full dose as planned, or an organ-at-risk may receive a higher dose than planned.

SUMMARY OF THE INVENTION

From the foregoing it is readily appreciated that there is a need for an improved MR imaging technique. It is consequently an object of the invention to provide a method that enables geometrically correct MR-only radiation therapy planning at minimum scan times.

In accordance with the invention, a method of MR imaging of a body of a patient positioned in an examination volume of an MR device is disclosed. The method comprises the steps of:

acquiring first MR imaging data representative of at least one region of the body;
analyzing said first MR imaging data to delineate at least one anatomical structure within said body region;
acquiring second MR imaging data of said body region using a multi-point Dixon sequence;
deriving a $B_0$ map from said second MR imaging data;
analyzing said $B_0$ map to determine at least one low fidelity region of said $B_0$ map;
performing $B_0$ mapping to refine the $B_0$ map using a multi-acquisition gradient echo sequence restricted to at least one region where said delineated anatomical structure and said low fidelity region overlap completely or partially; and
correcting geometrical distortions in said first and/or second MR imaging data using the refined $B_0$ map.

The invention proposes to acquire the first MR imaging data, for example using a $T_2$-weighted MR imaging sequence, which provides a suitable contrast for delineation of anatomical structures, such as tumors or organs-at-risk. The second MR imaging data are acquired using a multi-point Dixon method. This mDIXON data is used for the purpose of generating synthetic CT images in the MR-only radiation therapy planning workflow. The delineation of the anatomical structures can be transferred to the second MR imaging data (and to the resulting synthetic CT image) without loss of geometrical precision since the first and second MR imaging data are acquired by the same modality in the same frame of reference.

According to the known mDIXON technique, the spectral difference between fat and water protons is made use of for the purpose of separating MR signals emanating from water containing tissue and MR signals emanating from fat tissue. In mDIXON, multiple acquisitions of k-space are repeated with different echo times. The simplest mDIXON technique, 2-point Dixon, acquires two complete k-space data sets, wherein the fat magnetization in the second acquisition is out of phase relative to the first acquisition at the respective echo times. Separate and distinct water and fat images are obtained by simple addition or subtraction of the complex MR signal data sets. In general, a $B_0$ map, a water map and a fat map can be obtained by means of the mDIXON technique. Of particular advantage is that $B_0$ mapping using mDIXON is very fast and provides useful information regarding the water and fat distribution (in the form of the water map and the fat map) within the field of view in addition to the $B_0$ map. The $B_0$ map is exploited according to the invention for determining and correcting for geometrical image distortions caused by the spatial distribution of $B_0$.

An essential step of the method of the invention is the step of analyzing the mDIXON $B_0$ map to determine one or more low fidelity regions. As pointed out above, the mDIXON $B_0$ map lacks in fidelity only in very limited regions, whereby the precision of the $B_0$ map is completely sufficient in wide regions to correct the distortions with sufficient precision. It is therefore proposed to automatically identify those regions in which errors in the mDIXON based $B_0$ mapping and the related distortion estimation are large such that it will compromise dose planning. It is proposed to automatically perform dedicated $B_0$ mapping to refine the $B_0$ map using a gradient echo sequence restricted to at least one region in which said delineated anatomical structure and said low fidelity region overlap. In this way, the scan time consuming $B_0$ mapping is limited to the required minimum by acquiring the conventional $B_0$ map (using the multi-acquisition gradient echo sequence, in particular the dual acquisition gradient echo sequence) only in those regions being relevant for the radiation therapy planning, namely in those regions in which the mDIXON $B_0$ can be assumed to be of insufficient accuracy, but only as far as these low fidelity regions overlap with the regions to be treated by radiation therapy, namely the regions covered by the delineated anatomical structures.

The $B_0$ map refined in this way in the respective overlapping regions is finally used to correct the first and/or second MR imaging data such that a high level of geometrical accuracy is achieved at a minimum scan time.

In a preferred embodiment, the $B_0$ map is determined to be of low fidelity at positions where both the magnitude of the $B_0$ gradient and the magnitude of the geometrical distortion associated with $B_0$ are above respective predetermined thresholds. In this way, only those regions will be subject to refined $B_0$ mapping that will potentially lead to large errors in dose planning. These regions are characterized by a large geometrical distortion (i.e., a high $B_0$ deviation) and simultaneously a high spatial gradient of $B_0$ (i.e., a strong spatial variation of $B_0$). The respective thresholds can be selected by a user so as to achieve an optimum tradeoff between scan time and geometrical correctness.

The reduced fidelity of the $B_0$-map is markedly relevant for single-point or two-point mDixon imaging that employs a flexible echo spacing (i.e. other than in-phase and out-of-phase for the water and fat components of the magnetic resonance signal). Hence, in another implementation of the method of the invention, such a single-point mDixon or two-point mDixon sequence is combined with an at least three-point mDixon sequence to refine the $B_0$-map where said delineated anatomical structure and said low fidelity region completely or partially overlap.

In another preferred embodiment, a simulated CT image is computed from the corrected first and/or second MR imaging data by assigning a Hounsfield unit value to each pixel or voxel of the second MR imaging data. The simulated CT image is required for the actual dose calculation in the generation of the radiation therapy plan, because the CT image, with a Hounsfield Unit value assigned to each image position, provides the required radiation attenuation property of the imaged tissue. mDIXON imaging providing water/fat separation is known to be effective for the purpose of generating the synthetic CT images in the MR-only radiation therapy planning workflow (see references cited above). The simulated CT image may also be calculated based on the first MR imaging data, any further available MR imaging data or any combination of these. Any additional MR contrast information of the same region can be useful to determine the Hounsfield units for each image position.

In possible embodiments of the invention, the step of analyzing the first MR imaging data involves manual or automatic segmenting of the relevant anatomical structure (such as, e.g., a tumor or an organ-at-risk). When using automatic segmenting, the method of the invention can be performed in a fully automated fashion.

In yet another preferred embodiment, an overlay of the delineated anatomical structure with the determined low fidelity region of the $B_0$ map is displayed to the user. This informs the user of potential errors in dose planning. The user may react by adjusting the dose plan. This may be advisable in particular in regions where (parts of) the low fidelity regions intersect with the delineated tumor or organ-at-risk.

The method of the invention described thus far can be carried out by means of a MR device including at least one main magnet coil for generating a uniform, steady magnetic field $B_0$ within an examination volume, a number of gradient coils for generating switched magnetic field gradients in different spatial directions within the examination volume, at least one RF coil for generating RF pulses within the examination volume, one or more receiving coils for receiving MR signals from an object positioned in the examination volume, a control unit for controlling the temporal succession of RF pulses and switched magnetic field gradients, and a reconstruction unit. The method of the invention is implemented by a corresponding programming of the reconstruction unit and/or the control unit of the MR device.

The method of the invention can be advantageously carried out in most MR devices in clinical use at present. To this end it is merely necessary to utilize a computer program running on a computer by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF THE EMBODIMENTS

Figure 1:
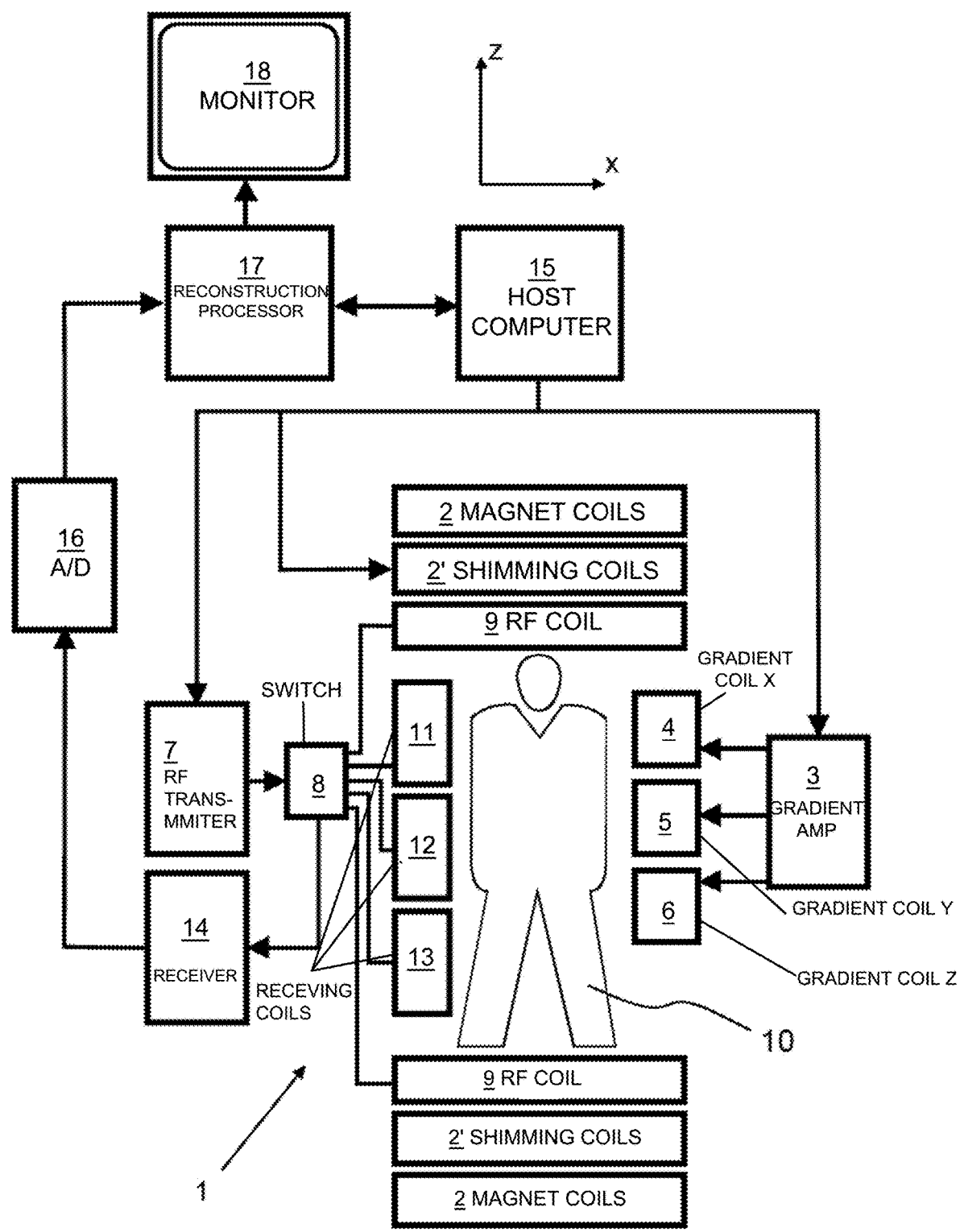
FIG. 1 shows a MR device for carrying out the method of the invention.

With reference to FIG. 1, a MR device 1 is shown. The device comprises superconducting or resistive main magnet coils 2 such that a substantially uniform, temporally constant main magnetic field $B_0$ is created along a z-axis through an examination volume. The device further comprises a set of shimming coils 2', wherein the current flow through the individual shimming coils of the set 2' is controllable for the purpose of minimizing $B_0$ deviations within the examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

More specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a body RF coil 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the body RF coil 9.

For generation of MR images of limited regions of the body 10, a set of local array RF coils 11, 12, 13 are placed contiguous to the region selected for imaging. The array coils 11, 12, 13 can be used as receiving coils to receive MR signals induced by body-coil RF transmissions.

The resultant MR signals are picked up by the body RF coil 9 and/or by the array RF coils 11, 12 and 13 and demodulated by a receiver 14 preferably including a preamplifier (not shown). The receiver 14 is connected to the RF coils 9, 11, 12 and 13 via send-/receive switch 8.

A host computer 15 controls the shimming coils 2' as well as the gradient pulse amplifier 3 and the transmitter 7 to generate any of a plurality of MR imaging sequences, such as echo planar imaging (EPI). For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modem MR devices, the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms, such like SENSE. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

Figure 2:
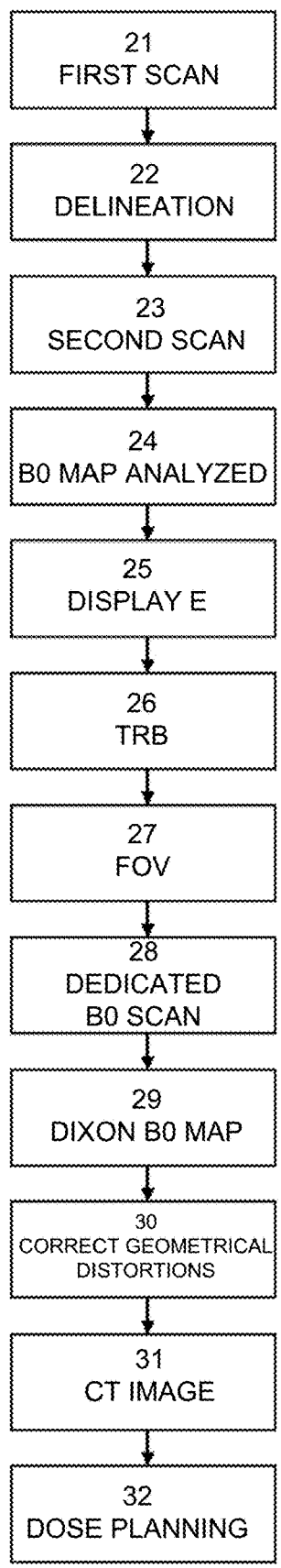
FIG. 2 schematically shows the method of the invention as a flow chart.
Figure 3:
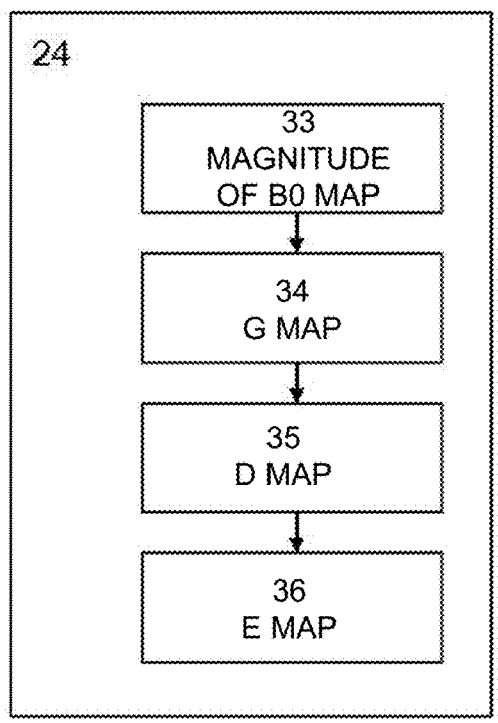
FIG. 3 schematically shows the process of analyzing the $B_0$ map to determine the low fidelity region as a flow chart.

An embodiment of the method of the invention is described with reference to FIGS. 2-4 and with further reference to FIG. 1 as follows:

After positioning the body 10 in the examination volume of the main magnet coil 2, a first MR imaging scan is started in step 21 for acquiring first MR imaging data, e.g. using a $T_2$-weighted scan. The first MR imaging data is representative of a region of the anatomy of body 10.

In step 22, a delineation of at least one anatomical structure, such as, e.g., a tumor to be treated or an organ-at-risk that should be prevented from being irradiated in radiation therapy, is performed either manually (e.g. by a radiologist interactively analyzing the first MR imaging data displayed on video monitor 18) or by a suitable auto-segmentation technique as it is per se known in the art. The result of the delineation may be a map (referred to in the following as TRB map) that covers only the borders of the delineated anatomical structure. The width of the borders may be a preset parameter depending on the type of tumor or organ-at-risk.

In step 23, second MR imaging data covering the same region of the anatomy of body 10 is acquired. A multi-point Dixon technique is employed for this purpose. Step 23 includes the derivation of a fat map, a water map and a $B_0$ map from the acquired mDIXON data.

In step 24, the derived $B_0$ map is analyzed to determine one or more low fidelity regions. This involves the steps depicted in FIG. 3. In step 33, the magnitude of the spatial gradient of the $B_0$ map is calculated for every image position. A map G is generated in step 34 covering all regions (i.e. indicating all image positions) in which this magnitude is larger than a pre-determined threshold. In step 35, a map D is calculated covering all regions in which the geometrical distortion resulting from the $B_0$ map at the respective image positions is larger than a further pre-determined threshold. A measure of the local geometrical distortion may be, e.g., the magnitude of a pixel/voxel shift caused by the respective local $B_0$ value. Finally, in step 36, a map $E=G \cap D$ is calculated which covers all regions that are covered by both maps G and D. E marks the image positions at which a low fidelity of the $B_0$ map can be expected. E covers only those regions in which the mDIXON $B_0$ map is known to be error prone. It can be expected that a geometrical correction based solely on the mDIXON $B_0$ map in these low fidelity regions would lead to significant errors in dose planning for radiotherapeutic treatment, because the geometrical distortion itself as well as its spatial variation are large.

An overlay of the low fidelity map E with the results of the delineation of anatomical structures in step 22 is displayed on video monitor 18 in step 25. This informs the user about potential errors in dose planning. The user may react by adjusting the dose plan which may be advisable in regions in which map E coincides with map TRB. In step 26, a map $R=E \cap TRB$ is calculated indicating the image regions where the delineated anatomical structures and the low fidelity region of the $B_0$ map overlap (completely or partially), i.e. error prone regions of the $B_0$ map at the border of a tumor or an organ-at-risk.

A field of view is determined in step 27 that covers map R. The field of view may be subdivided into several distinct regions. In step 28, an automated dedicated $B_0$ mapping scan using a multi-acquisition gradient echo imaging sequence is performed for the determined field of view. The $B_0$ mapping scan may consist of several sub-scans each addressing a different region of the field of view.

The mDIXON $B_0$ map is then updated in step 29 accordingly in the regions indicated by map R by replacing the $B_0$ values of the mDIXON $B_0$ map by the corresponding values obtained from the dedicated $B_0$ mapping scan in these regions. The result is a refined, i.e. higher fidelity $B_0$ map.

In step 30, the refined $B_0$ map is then used to correct geometrical distortions in the first and second MR imaging data.

A simulated CT image is computed in step 31 from the distortion-corrected second MR imaging data. This involves assigning a Hounsfield Unit value to each pixel or voxel of the second MR imaging data.

In step 32, the user/radiologist performs dose planning for radiation therapy using the simulated CT image as well as the geometrically corrected first MR imaging data. In case of auto-segmentation being used for the delineation of tumors and organs-at-risk in step 22, all steps 21-31 can be performed fully automatically. In particular, this enables automatic acquisition of the $B_0$ map update on the fly directly after the mDIXON scan. This means that the patient does not have to stay in the examination volume of the MR device 1. Patient throughput can thus be maximized.

It has further to be noted that in typical cases only very few or even no regions at all will be contained in map R. This means that the additional acquisition time required for the dedicated $B_0$ mapping scan is either zero or at least very small. Therefore, the approach proposed by the invention combines both, high precision in distortion correction and very short acquisition time if compared to conventional $B_0$ mapping for the full field of view.

Figure 4:
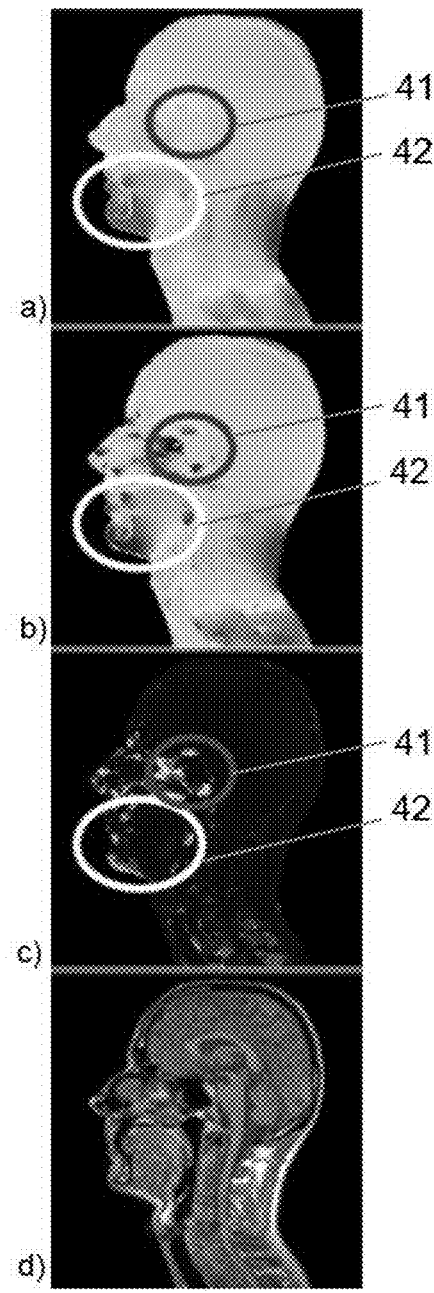
FIG. 4 shows MR image data illustrating the background of the approach of the invention.

FIG. 4 shows examples of sagittal slices of MR image data of the head/neck region. The image values of the two top images (FIGS. 4a and 4b) indicate the local geometrical image distortion (the magnitude of the $B_0$-induced voxel shift). The top image (FIG. 4a) shows the geometrical distortion derived from the mDIXON $B_0$ map. The image below (FIG. 4b) shows the geometrical distortion derived from conventional dedicated $B_0$ mapping. The third image of FIG. 4c shows the difference of the two images of FIGS. 4a and 4b. The image of FIG. 4d is the mDIXON in-phase image shown as an anatomical reference. As can be seen, geometrical distortions are well estimated by mDIXON in regions with low spatial variation (e.g. region indicated by white circle 42). Differences exceeding 50% occur in regions with high spatial variation of $B_0$ (circle 41). As can be seen in FIG. 4, the mDIXON $B_0$ map is of low fidelity mostly around nasal, oral, and ear cavities, the sphenoid sinus and dental fillings. If a tumor to be treated by radiation therapy or an organ-at-risk to be prevented from being irradiated is within one of these regions there is a significant risk of misalignment and erroneous dose calculation if the geometrical correction is based solely on the mDIXON $B_0$ map. To this end, the invention proposes to refine the mDIXON $B_0$ map in a targeted fashion only in the relevant regions.

The invention claimed is:

1. A method of magnetic resonance (MR) imaging of a body of a patient positioned in an examination volume of an MR device, the method comprising:
    acquiring first MR imaging data representative of at least one region of the body;
    analyzing said first MR imaging data to delineate at least one anatomical structure within said at least one region of the body;
    acquiring second MR imaging data of said at least one body region using a multi-point Dixon sequence;
    deriving a BO map from said second MR imaging data;
    analyzing said BO map to determine at least one low fidelity region of said BO map;
    performing BO mapping to refine the BO map using a multi-acquisition gradient echo sequence, comprising a dual acquisition gradient echo sequence restricted to at least one region where said delineated anatomical structure and said low fidelity region overlap completely or partially; and
    correcting geometrical distortions in said first and/or second MR imaging data using the refined BO map.

2. The method of claim 1, wherein the BO map is determined to be of low fidelity at positions where both the magnitude of the BO gradient and the magnitude of the geometrical distortion associated with BO are above respective predetermined thresholds.

3. The method of claim 1 wherein a simulated computed tomography (CT) image is computed from at least one of the corrected first or second MR imaging data by assigning a Hounsfield Unit value to each pixel or voxel of the second MR imaging data.

4. The method of claim 3, wherein a radiation therapy plan is generated using the simulated CT image.

5. The method of claim 1, wherein said analyzing of said first MR imaging data involves automatic segmenting of said anatomical structure.

6. The method of claim 1, wherein an overlay of said delineated anatomical structure with said low fidelity region is displayed.

7. A method of magnetic resonance (MR) imaging of a body of a patient positioned in an examination volume of an MR device, the method comprising:
    acquiring first MR imaging data representative of at least one region of the body;
    analyzing said first MR imaging data to delineate at least one anatomical structure within said at least one region of the body;
    acquiring second MR imaging data of said at least one region of the body using a single-point or two-point Dixon sequence;
    deriving a BO map from said second MR imaging data;
    analyzing said BO map to determine at least one low fidelity region of said BO map;
    performing BO mapping to refine the BO map using an at least three-point Dixon sequence restricted to at least one region where said delineated anatomical structure and said low fidelity region overlap completely or partially; and
    correcting geometrical distortions in said first and/or second MR imaging data using the refined BO map.

8. A magnetic resonance (MR) device including at least one main magnet coil to generate a uniform, steady magnetic field BO within an examination volume, a number of gradient coils configured to generate switched magnetic field gradients in different spatial directions within the examination volume, at least one RF coil configured to generate radio frequency (RF) pulses within the examination volume, one or more receiving coils configured to receive MR signals from a body of a patient, a controller configured to control the temporal succession of RF pulses and switched magnetic field gradients, and a reconstruction processor, wherein the MR device is configured to acquire first MR imaging data representative of at least one region of the body;
    analyze said first MR imaging data to delineate at least one anatomical structure within said at least one region of the body;
    acquire second MR imaging data of said at least one body region using a multi-point Dixon sequence;
    derive a BO map from said second MR imaging data;
    analyzing said BO map to determine at least one low fidelity region of said BO map;
    perform BO mapping to refine the BO map using a multi-acquisition gradient echo sequence or an at least three-point Dixon sequence restricted to the at least one region of the body in which said delineated anatomical structure and said low fidelity region overlap; and
    correct geometrical distortions in said first and/or second MR imaging data using the refined BO map.

9. The MR device of claim 8, wherein the BO map is determined to be of low fidelity at positions where both the magnitude of the BO gradient and the magnitude of the geometrical distortion associated with BO are above respective predetermined thresholds.

10. The MR device of claim 8, wherein the MR device is further configured to compute a simulated computed tomography (CT) image from at least one of the corrected first or second MR imaging data by assigning a Hounsfield Unit value to each pixel or voxel of the second MR imaging data.

11. The MR device of claim 10, wherein the MR device is further configured to generate a radiation therapy plan using the simulated CT image.

12. The MR device of claim 8, wherein the MR device is further configured to automatically segment the anatomical structure when the first MR imaging data are analyzed.

13. The MR device of claim 8, wherein the MR device is further configured to overlay the delineated anatomical structure with said low fidelity region on a display.

14. A non-transitory computer readable medium having instructions stored thereon, which when executed by a processor cause a magnetic resonance (MR) device to:

acquire first MR imaging data representative of at least one region of the body;

analyze said first MR imaging data to delineate at least one anatomical structure within said at least one region of the body;

acquire second MR imaging data of said at least one region of the body using a multi-point Dixon sequence;

derive a BO map from said second MR imaging data;

analyze said BO map to determine at least one low fidelity region of said BO map;

perform BO mapping to refine the BO map using a multi-acquisition gradient echo sequence, comprising a dual acquisition gradient echo sequence restricted to at least one region where said delineated anatomical structure and said low fidelity region overlap completely or partially; and correct geometrical distortions in said first and/or second MR imaging data using the refined BO map.

15. The non-transitory computer readable medium of claim 14, wherein the BO map is determined to be of low fidelity at positions where both the magnitude of the BO gradient and the magnitude of the geometrical distortion associated with BO are above respective predetermined thresholds.

16. The non-transitory computer readable medium of claim 14, wherein the instructions further cause the processor to compute a simulated computed tomography (CT) image is computed from at least one of the corrected first or second MR imaging data by assigning a Hounsfield Unit value to each pixel or voxel of the second MR imaging data.

17. The non-transitory computer readable medium of claim 16, wherein the instructions further cause the processor to generate a radiation therapy plan using the simulated CT image.

18. The non-transitory computer readable medium of claim 14, wherein the instructions further cause the processor to automatically segment the anatomical structure when the first MR imaging data are analyzed.

19. The non-transitory computer readable medium of claim 14, wherein the instructions further cause the processor to overlay the delineated anatomical structure with said low fidelity region on a display.

* * * * *